(12) United States Patent
Byrne

(10) Patent No.: US 7,943,391 B1
(45) Date of Patent: May 17, 2011

(54) METHOD OF PERFORMING IN SITU CALIBRATED POTENTIOMETRIC PH MEASUREMENTS

(75) Inventor: Robert H. Byrne, St. Petersburg, FL (US)

(73) Assignee: University of South Florida, Tampa, FL (US)

(*) Notice: Subject to any disclaimer, the term of this patent is extended or adjusted under 35 U.S.C. 154(b) by 236 days.

(21) Appl. No.: 12/180,021

(22) Filed: Jul. 25, 2008

Related U.S. Application Data

(63) Continuation-in-part of application No. 12/110,730, filed on Apr. 28, 2008, now Pat. No. 7,842,507.

(60) Provisional application No. 60/914,384, filed on Apr. 27, 2007.

(51) Int. Cl.
*G01N 31/16* (2006.01)
(52) U.S. Cl. .................................... 436/163; 436/164
(58) Field of Classification Search .................. 436/163, 436/164
See application file for complete search history.

(56) References Cited

OTHER PUBLICATIONS

Spectrophotometric Determination of Freshwater pH Using Bromocresol Purple and Phenol Red Wensheng Yao and Robert Byrne Environmental Science and Technology, 2001, 35, 1197-1201.*

Redundant Chemical Sensors for Calibration-Impossible Applications J.C. Seiter and M.D. DeGrandpre Talanta 54 (2001) 99-106.*

* cited by examiner

*Primary Examiner* — Jill Warden
*Assistant Examiner* — Dwan A Gerido
(74) *Attorney, Agent, or Firm* — Michele L. Lawson; Smith & Hopen, P.A.

(57) ABSTRACT

A device for the precise and accurate potentiometric pH measurements in situ. Embodiments of a potentiometric device according to the invention consist of one or more glass pH-sensitive electrodes connected to a potentiometer. A key feature of the device is that, rather than being calibrated conventionally with buffers, it can be calibrated with an in situ device that measures pH spectrophotometrically. Spectrophotometric pH measurements obtained via sulfonephthalein absorbance measurements are inherently calibrated (do not require buffers). Thus, devices according to the invention allow for continuous potentiometric pH measurements with occasional spectrophotometric calibrations. The spectrophotometric calibration device consists of a spectrophotometer with associated pumps for combining a sulfonephthalein pH indicator with the aqueous medium whose pH is to be measured. The device will record potentiometric pH measurements for an extended period of time until the spectrophotometric device is autonomously activated for another calibration. In this manner precise and accurate pH measurements can be obtained continuously in the environment, and the low energy expenditure of the potentiometric device provides excellent endurance. Also provided is a method and associated devices for spectrophotometrically determining the salinity of an aqueous medium.

2 Claims, 12 Drawing Sheets

METHOD OF PERFORMING IN SITU CALIBRATED POTENTIOMETRIC PH MEASUREMENTS

CROSS REFERENCE TO RELATED APPLICATIONS

This application is a continuation-in-part of prior U.S. patent application Ser. No. 12/110,730, entitled "Sensor for Direct Measurement of Carbonate Ions in Sea Water" filed on Apr. 28, 2008, which claims the benefit of priority to U.S. Provisional Patent Application 60/914,384, entitled, "Sensor for Direct Measurement of Carbonate Ions in Sea Water", filed Apr. 27, 2007, the contents of which applications are herein incorporated by reference.

STATEMENT OF GOVERNMENT INTEREST

This invention was made with Government support under Grant Nos. OCE-0551676 and N00014-03-1-0612 awarded by the National Science Foundation and Office of Naval Research, respectively. The Government has certain rights in the invention.

FIELD OF INVENTION

This invention relates to sensors for extended deployment in aquatic environments. More specifically, this invention relates to devices and associated methods for precise and accurate potentiometric pH measurements in situ over periods of extended deployment with occasional spectrophotometric calibrations.

BACKGROUND OF THE INVENTION

Solution pH is widely conceptualized as a master variable in the regulation of natural aqueous systems. It is a key feature in descriptive models of carbonate system chemistry, trace metal speciation and bioavailability, oxidation-reduction equilibria and kinetics, biologically induced carbon system transformations, and the aqueous interactions and transformations of minerals. Rising levels of atmospheric $CO_2$ are leading to ocean acidification. The response of seawater and freshwaters to acidification processes has created a need for autonomous global monitoring of ocean water and fresh water pH. The importance of pH in investigations of terrestrial and oceanic biogeochemistry has necessitated improvements in not only the quality of measurements (precision and accuracy), but also the spatial and temporal resolution of measurements in the field. Potentiometric devices are rarely used for in situ environmental pH measurements because in situ buffer calibrations are problematic. Spectrophotometric devices have been developed for in situ environmental measurements but the endurance and measurement frequency of spectrophotometric devices is relatively low due to high power requirements and the limited longevity of lamps. Achieving meaningful spatial and temporal measurements in the field mandates the introduction of robust measurement devices capable of accurate and precise measurements over extended timeframes.

SUMMARY OF THE INVENTION

The present invention provides a device capable of precise and accurate potentiometric pH measurements in situ. Also provided are associated methods for in situ calibrated pH measurements. Embodiments of an in situ calibrated potentiometric device according to the invention couple potentiometric pH measurement systems to systems for calibrating the potentiometric pH measurement systems. The potentiometric system/aspect of the device employs one or more glass pH-sensitive electrodes connected to a potentiometer (i.e., a device capable of measuring electrical potentials [voltages]). A key feature of the potentiometric system is that, rather than being calibrated conventionally with buffers, it can be calibrated with an in situ device that measures pH spectrophotometrically. Spectrophotometric pH measurements obtained via sulfonephthalein absorbance measurements are inherently calibrated and do not require the buffers necessary for the calibration of typical potentiometric devices. Thus, devices according to the invention allow for continuous potentiometric pH measurements with occasional spectrophotometric calibrations.

The spectrophotometric calibration system/aspect of the device utilizes a spectrophotometer with associated pumps for combining a sulfonephthalein pH indicator with the aqueous medium whose pH is to be measured. After a sulfonephthalein indicator and the aqueous medium (e.g., seawater) are combined in an optical cell, light is passed through the combined mixture, an absorbance spectrum is obtained and solution pH is calculated from (a) optical absorbance ratios at multiple wavelengths, (b) temperature, and (c) the salt concentration (e.g., salinity) of the solution. Through contemporaneous potentiometric measurements, the potentiometric pH system (glass electrode plus volt meter) is calibrated without the use of buffers. The device will record potentiometric pH measurements for an extended period of time until the spectrophotometric device is autonomously activated for another calibration. In this manner precise and accurate pH measurements can be obtained continuously in the environment, and the low energy expenditure of the potentiometric device provides excellent endurance.

In a first aspect the present invention provides a device for in situ calibrated potentiometric pH measurement. The device includes a potentiometric pH measurement module, a spectrophotometric pH measurement module and a calibration module. The calibration module is in communication with the potentiometric pH measurement module and the spectrophotometric pH measurement module. The calibration module receives pH calibration data from the potentiometric pH measurement module and the spectrophotometric pH measurement module and performs calibrations to the potentiometric pH measurement module using the received pH calibration data.

In certain embodiments the received pH calibration data utilizes one or more substantially contemporaneous pH measurements from the potentiometric pH measurement module and the spectrophotometric pH measurement module. Thus, a potentiometric pH measurement is performed at substantially simultaneously to a spectrophotometric pH measurement. By performing the operations coextensively, fluctuations due to ambient conditions and sample identity are minimized.

In further embodiments of the device the spectrophotometric pH measurement module can include a first reservoir containing a sulfonephthalein pH indicator, one or more pumps in communication with the first reservoir and an aqueous medium, a second reservoir to receive combined aqueous medium/pH indicator (combined mixture), and a spectrophotometer to measure the absorbance characteristics of the combined mixture. The one or more pumps combine a sulfonephthalein pH indicator with the aqueous medium. In an advantageous embodiment of the device the calibration module can include systems for the autonomous activation of the calibration module. The calibration module can be autonomously activated upon a defined time interval or at an event trigger indicating the necessity for calibration of the potentiometer. The potentiometric pH measurement module can include one or more glass pH-sensitive electrodes connected to a potentiometer. The device according to claim 5 wherein the calibration module is autonomously activated upon a defined time interval or at an event trigger indicating the necessity for calibration of the potentiometer.

In certain embodiments the device can include a housing containing the potentiometric pH measurement module, the spectrophotometric pH measurement module and the calibration module in communication. The housing can have one or more sample intake ports and one or more sample exhaust ports to allow the intake and exhaust of the samples. The housing can also be sealed to allow operation while partially or totally immersed in an aqueous medium.

In a second aspect the present invention provides a device for autonomously-activated in situ calibrated potentiometric pH measurement. The device includes a potentiometric pH measurement module, a spectrophotometric pH measurement module, and an autonomously-activated calibration module. The autonomously-activated calibration module is in communication with the potentiometric pH measurement module and the spectrophotometric pH measurement module. The calibration module receives pH calibration data from the potentiometric pH measurement module and the spectrophotometric pH measurement module and performs calibrations to the potentiometric pH measurement module using the received pH calibration data. The autonomously-activated calibration module can be activated upon a defined time interval or at an event trigger indicating the necessity for calibration of the potentiometer.

In certain embodiments of the device the spectrophotometric pH measurement module can include a first reservoir containing a sulfonephthalein pH indicator, one or more pumps in communication with the first reservoir and an aqueous medium a second reservoir to receive combined aqueous medium/pH indicator (combined mixture), and a spectrophotometer to measure the absorbance characteristics of the combined mixture. The one or more pumps combine a sulfonephthalein pH indicator with the aqueous medium.

In a third aspect the present invention provides a method of performing in situ calibrated potentiometric pH measurements for extended periods of time. The method includes the steps of recording a plurality of potentiometric pH measurements using a potentiometric pH measurement device, activating a spectrophotometric calibration system, spectrophotmetrically calibrating the potentiometric pH measurement device, and resetting the activator of the spectrophotometric calibration system to allow the potentiometric pH measurement device to return to recording potentiometric pH measurements. The spectrophotometric calibration system can be autonomously activated. The autonomous activation can occur upon a defined time interval or at an event trigger indicating the necessity for calibration.

In certain embodiments the step of spectrophotmetrically calibrating the potentiometric pH measurement device includes the steps of sampling an aqueous medium, accessing data representative of the temperature and salt concentration of the sampled aqueous medium, combining a sulfonephthalein indicator and a first portion of the sampled aqueous medium, delivering the combined medium to an optical cell, obtaining an absorbance spectrum from the combined medium, calculating solution pH of the sampled aqueous medium utilizing the optical absorbance ratios at multiple wavelengths, the temperature, and the salt concentration, obtaining a potentiometric pH measurement of a second portion of the aqueous medium, calculating the deviation between the potentiometric pH measurement and the spectrophotometric pH measurement, and adjusting the potentiometric pH measurement device using the calculated deviation. The spectrophotometric pH measurement is considered accurate, while any deviation between the potentiometric pH measurement and the spectrophotometric pH measurement is due to discrepencies in the potentiometric pH measurement due to factors such as the inherent drift observed in this type of unit over time. The adjusting step calibrates the potentiometric pH measurement device.

In certain embodiments the step of obtaining a potentiometric pH measurement of a second portion of the aqueous medium is performed substantially contemporaneously with the step of obtaining an absorbance spectrum from the combined medium.

In a fourth aspect the present invention provides a method of spectrophotmetrically calibrating a potentiometric pH measurement device. The method includes the steps of obtaining one or more samples of an aqueous medium, accessing data representative of the temperature and salt concentration of the sampled aqueous medium, combining a sulfonephthalein indicator and a first portion of the sampled aqueous medium, delivering the combined medium to an optical cell, obtaining an absorbance spectrum from the combined medium and calculating solution pH of the sampled aqueous medium utilizing the optical absorbance ratios at multiple wavelengths, the temperature, and the salt concentration, obtaining a potentiometric pH measurement of a second portion of the aqueous medium, calculating the deviation between the potentiometric pH measurement and the spectrophotometric pH measurement, and adjusting the potentiometric pH measurement device using the calculated deviation. The adjusting step calibrates the potentiometric pH measurement device.

In certain embodiments the step of obtaining a potentiometric pH measurement of a second portion of the aqueous medium is performed substantially contemporaneously with the step of obtaining an absorbance spectrum from the combined medium. In additional embodiments the method of spectrophotmetrically calibrating the potentiometric pH measurement can be autonomously activated. Autonomous activation can occurs upon a defined time interval or at an event trigger indicating the necessity for calibration or under other conditions.

In a fifth aspect the present invention provides a method of measuring the salinity of an aqueous solution, the method includes the steps of obtaining a sample of an aqueous medium, adding a metal ion species the aqueous medium to produce a sample solution, spectrophotometrically measuring the absorbance of light passing through the sample solution at a plurality of wavelengths, wherein the ultraviolet absorbance of light is a function of the complexation in the sample solution of the added metal ion species with carbonate ions of the sample and computing the salinity of the aqueous medium based upon the absorbance ratio of the sample solution at the plurality of wavelengths.

In certain embodiments the spectrophotometric absorbance measurements are obtained in the ultraviolet range.

In certain embodiments the metal ion can include $Pb^{II}$ and $Cu^{II}$, yttrium, a lanthanide metal and an actinide metal. In embodiments where the metal ion species is $Pb^{II}$, one of the plurality spectrophotometric absorbance measurements used to calculate the absorbance ratio can be measured at about $\lambda=234$ nm In further aspects of this embodiment a second of the plurality of spectrophotometric absorbance measurements used to calculate the absorbance ratio is measured at about λ=240 nm. to about λ=260 nm In still further aspects, the metal ion species is $Pb^{II}$ and the spetrophotometric absorbance measurements are measured at about λ=234 nm. and about λ=250 nm.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
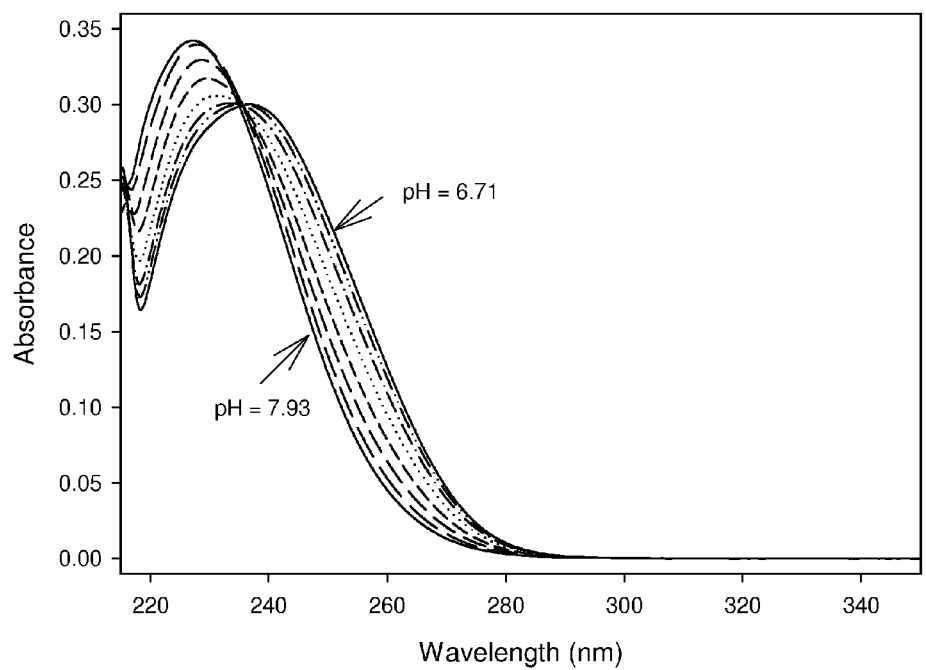
FIG. 1 is a graph showing Pb(II) UV absorbance spectra in seawater at S=35.87 and 25° C. as a function of pH.

Rising levels of atmospheric $CO_2$ are leading to ocean acidification. The response of seawater and freshwaters to acidification processes has created a need for autonomous global monitoring of ocean water and fresh water pH. Potentiometric devices are rarely used for in situ environmental pH measurements because in situ buffer calibrations are problematic. Spectrophotometric devices have been developed for in situ environmental measurements but the endurance and measurement frequency of spectrophotometric devices is relatively low due to high power requirements and the limited longevity of lamps. Spectrophotometric and potentiometric devices can be combined to reduce power, enhance longevity and still provide high quality calibrated measurements.

Both potentiometric and spectrophotometric procedures can be used for pH measurements. Potentiometric pH measurements can be performed with relatively simple equipment and procedures required. This simplicity makes potentiometry a good choice for field measurements as long as there are not stringent requirements for accuracy and precision. Under ideal conditions, potentiometric measurements that utilize glass hydrogen ion selective electrodes can provide measurement precisions on the order of 0.003 pH units. However, measurement accuracy can be problematic. Potentiometric measurements generally require regular buffer calibrations, and special care must be taken to address artifacts associated with both residual liquid junction potentials and variations in asymmetry potentials. Seiter and DeGrandpre evaluated performance of six electrodes under identical operational conditions. They observed that individual electrodes generally have distinctive drift patterns, with drift rates up to 0.02 pH units per day (Seiter, J. C.; DeGrandpre, M. D. *Talanta* 2001, 54, 99). Electrode drift necessitates frequent calibrations, making autonomous operation somewhat problematic compared to spectrophotometric pH determinations. One important advantage of potentiometric devices is their low power consumption. This aspect would seem to make them well-suited for deployment over extended periods of time. Unfortunately, their use for such deployment is greatly limited by their inherent drift, making readings increasingly inaccurate and necessitating calibration for meaningful use.

Although potentiometric pH measurements are versatile and satisfactory for many applications, spectrophotometric pH measurement procedures have at least two important advantages that make them particularly desirable. Since spectrophotometric pH measurements can be determined via absorbance ratios, and the calibration of pH indicators is a laboratory exercise that establishes how each indicator's molecular properties vary with temperature, pressure and ionic strength, spectrophotometric pH measurements are inherently calibrated and can be termed "calibration free". Subsequent to careful laboratory calibration, spectrophotometric pH measurements do not require the use of buffers. Secondly, thousands of at-sea observations have demonstrated that the imprecision of shipboard spectrophotometric pH measurements is on the order of 0.0003 to 0.0004 pH units, approximately an order of magnitude better than potentiometric results. These advantageous attributes of spectrophotometric pH measurements have made spectrophotometric procedures valuable for not only observations of pH, but also for measurements of $CO_2$ fugacity and total dissolved inorganic carbon. However, the power consumption of spectrophotometers is considerably greater than potentiometers. This can be a limitation for their long-term deployment. The limited longevity of lamps in spectrophotometers is an additional impediment to their long-term deployment.

Spectrophotometric pH measurements have been increasingly utilized for measurements of pH in natural waters. Bellerby et al. developed a flow injection procedure for spectrophotometric measurement of seawater pH with a reported precision of 0.005 pH units and a sample frequency of 25 $hr^{-1}$ (Bellerby R. G. J.; Turner, D. R.; Millward, G. E.; Worsfold P. J. *Analytica Chimica Acta* 1995, 309, 259.). Tapp et al. described the use of a shipboard system for spectrophotometric measurements of surface water pH with a reported precision on the order of 0.001 pH units and a 1-Hz measurement frequency (Tapp, M.; Hunter, K.; Currie, K.; Mackaskill, B. *Mar. Chem.* 2000, 72, 193.). Relative to discrete measurements however, observed discrepancies were as large as 0.02 pH units. Martz et al. described the construction of a submersible pH sensor with a 0.003 unit measurement precision and a measurement frequency of 6 $hr^{-1}$ (Martz, T. R.; Carr, J. J.; French, C. R.; DeGrandpre, M. D. Anal. Chem. 2003, 75, 1844.).

Submersible potentiometric sensors according to the present invention provide continuous unattended measurements of seawater pH for periods of six to twelve months with a measurement frequency up to 60 Hz. No calibrations are required on the part of the user. Both measurements and calibrations are performed in-situ. Measurement accuracy is on the order of 0.001 pH units. High measurement frequency, excellent endurance characteristics, and in situ calibration make this sensor system well suited to descriptions of acid-base equilibrium and kinetic phenomena on diurnal, seasonal and annual scales.

The present invention provides a device capable of precise and accurate potentiometric pH measurements in situ. Embodiments of a potentiometric device according to the invention consist of one or more glass pH-sensitive electrodes connected to a potentiometer (e.g., a device capable of measuring electrical potentials [voltages]). A key feature of the device is that, rather than being calibrated conventionally with buffers, it can be calibrated with an in situ device that measures pH spectrophotometrically. Spectrophotometric pH measurements obtained via sulfonephthalein absorbance measurements are inherently calibrated (do not require buffers). Thus, devices according to the invention allow for continuous potentiometric pH measurements with occasional spectrophotometric calibrations. The spectrophotometric calibration device consists of a spectrophotometer with associated pumps for combining a sulfonephthalein pH indicator with the aqueous medium whose pH is to be measured. After a sulfonephthalein indicator and the aqueous medium (e.g., seawater) are combined in an optical cell, light is passed through the combined mixture, an absorbance spectrum is obtained and solution pH is calculated from (a) optical absorbance ratios at multiple wavelengths, (b) temperature, and (c) the salt concentration (e.g., salinity) of the solution. Through contemporaneous potentiometric measurements the potentiometric pH system (glass electrode plus volt meter) is calibrated without the use of buffers. The device will record potentiometric pH measurements for an extended period of time until the spectrophotometric device is autonomously activated for another calibration. In this manner precise and accurate pH measurements can be obtained continuously in the environment, and the low energy expenditure of the potentiometric device provides excellent endurance.

It is contemplated that calibrations can be triggered by a variety of events or circumstances. For example, calibrations can be triggered based upon time intervals or other user-defined events. Alternatively, or in conjunction with such tachniques, calibrations can be triggered based upon observations of potentiometric pH changes. For example, a sudden pH cahnge outside of the typical deviations of pH recordings could trigger a calibration to ensure that the large recorded deviaiton was real.

A number of other solutions are available to avoid problems associated with potiometric drift in the long-term deployment of these devices. Pontiometric pH measurement devices consist of (a) a glass pH sensitive membrane and (b) a reference electrode. One of the main sources problems in a potentiometric pH measurement is clogging of what is called the 'liquid junction' of the reference cell. This is an event that could initiate drift. If the potentiometric system is initially calibrated, some slow drift may be acceptable because subsequent deviations between spectrophotometric and potentiometric measurements might be small. If deviations suddenly become large, the device could be told to select a different reference electrode (or a different glass electrode). Alternatively, or in conjunctions with the above procedures, the system could be directed to flush itself with a microbial inhibitor or to activate an ultrasonic device for cleaning.

Procedures for direct measurements of carbonate ion concentrations and saturation states in seawater have also been developed. Measurements are obtained via ultraviolet spectroscopic observations of Pb(II) spectra as the relative concentrations of $PbCO_3^0$ and an ensemble of lead chloride complexes vary in response to dissolved $CO_3^{2-}$. Measurement precision is enhanced by parameterization in terms of absorbance ratios. The $PbCO_3^0$ stability constant, and Pb(II) molar absorbance ratios in seawater, were determined at 25° C. over a range of salinity between 36 and 20. The procedures described herein are well suited to measurements throughout the normal range of carbonate ion concentrations in the oceans. Rapid equilibration rates for Pb(II) carbonate complexation make the procedures described in this work well suited to rapid direct analysis in situ.

The health of coral reefs and calcareous plankton is also strongly influenced by the carbonate saturation state of seawater. Calculations of carbonate saturation states currently require measurements of two $CO_2$ system parameters, such as pH and total dissolved carbon, plus thermodynamic calculations that relate carbonate ion concentrations to directly measured parameters.

Investigations of the marine $CO_2$ system are commonly conducted through measurements of four primary variables: total dissolved inorganic carbon ($C_T$), total solution alkalinity ($A_T$), $CO_2$ fugacity ($fCO_2$), and solution pH. Thermodynamic models link these four primary variables, whereby measurements of any two variables can be used to calculate the two remaining parameters (DOE, 1994). These models also allow calculations of the concentrations of the individual forms of inorganic carbon in seawater: the dissolved concentrations of $CO_2$ and $H_2CO_2$, and the free plus ion paired concentrations of bicarbonate, $HCO_3^-$, and carbonate, $CO_3^{2-}$. Two of the directly measured and derived $CO_2$ system variables can be highlighted because of their special significance in evaluations of global carbon fluxes and the biogeochemistry of marine carbonates in general. $CO_2$ fugacity measurements are essential to descriptions of $CO_2$ exchange at the air sea interface (DOE, 1994; McGillis and Wanninkhof, 2006; Millero, 2007), and carbonate ion concentrations are essential to evaluations of (a) the mineralization rates of marine calcifiers (Langdon and Atkinson, 2005) and (b) the dissolution rates of calcite and aragonite ($CaCO_{3(s)}$ polymorphs) both on the seafloor and in the water column (Morse, 1978; Keir, 1980; Acker et al., 1987).

Rising atmospheric carbon dioxide concentrations over the past two centuries have led to increasing $CO_2$ uptake by the oceans (Royal Society, 2005). This process, which is decreasing the pH of the upper ocean, is reducing oceanic carbonate ion concentrations and thus the level of saturation of calcium carbonate (Broecker et al, 1979; Feely et al., 2004; On et al., 2005). If the trend continues, it will have a seriously negative impact on key marine organisms such as corals and some plankton (Kleypas et al, 2006). In view of the importance of carbonate ion concentrations ($[CO_3^{2-}]_T$) to the oceans' rapidly evolving carbonate system, it is then highly desirable to move $[CO_3^{2-}]_T$ from the rank of derived $CO_2$ system variables to the list of primary measured variables.

A variety of metals in seawater, including lead (Byrne, 1981), copper (Byrne and Miller, 1985), the lanthanides (Cantrell and Byrne, 1987), and various actinides (Byrne, 2002) have inorganic speciation schemes that are strongly dominated by carbonate complexation. Among these metals, the speciation of Pb(II) and Cu(II) has been examined directly by ultraviolet absorbance spectroscopy in natural seawater (Byrne, 1981; Byrne and Miller, 1985). Since the ultraviolet absorbance characteristics of these metals are strongly influenced by dissolved carbonate, it follows that observations of Pb(II) and Cu(II) absorbance spectra can be used to directly determine seawater carbonate ion concentrations. As a means of achieving high precisions in such determinations, we have developed procedures that involve measurements of absorbance ratios rather than absolute absorbance. Our techniques are closely analogous to those that were developed previously for seawater pH measurements with precisions on the order of 0.0004 pH units (Robert Baldo et al, 1985; Byrne, 1987; Byrne and Breland, 1989; Clayton and Byrne, 1993). Whereas spectrophotometric observations of sulfonephthalein acid/base equilibria are utilized for seawater pH measurements, spectrophotometric observations of metal ion complexation can be used to quantify anion concentrations in seawater. Lead is especially well suited to such measurements because (a) $PbCO_3^0$ and a variety of Pb(II) chloride complexes have dissimilar absorbance spectra in the ultraviolet, and (b) species other than $PbCO_3^0$ and chloride complexes appear to be insignificant over a wide range of salinities in natural seawater. In this work, Pb(II) formation constants and molar absorbance ratios required for direct determinations of carbonate ion concentrations in seawater are characterized at 25° C. as a function of salinity. In addition to development of procedures for measurement of carbonate ions and carbonate saturation state, we also show that measurements of Pb(II) absorbance ratios in acidified seawater can be used to determine seawater salinity with a precision on the order of ±0.1 salinity units. The procedures described in this work are suitable for rapid autonomous in-situ monitoring of carbonate ion concentration in seawater.

Theoretical Principles

The $PbCO_3^0$ formation reaction in seawater, $$Pb^{2+} + CO_3^{2-} \leftrightarrow PbCO_3^0, \quad (1)$$

can be quantitatively described with an equilibrium constant of the following form:

$$_{CO3}\beta_1 = \frac{[PbCO_3^0]_T}{[Pb_T][CO_3^{2-}]_T} \quad (2)$$

where $[Pb_T]$ represents the total concentration of Pb(II) species other than $PbCO_3^0$ in seawater, principally $Pb^{2+}$, $PbCl^+$, $PbCl_2^0$ and $PbCl_3^-$, and minor amounts of $PbSO_4^0$; $[CO_3^{2-}]_T$ is the sum concentration of free and ion paired carbonate ($CO_3^{2-}$, $NaCO_3^-$, $MgCO_3^0$ and $CaCO_3^0$; and $[PbCO_3^0]_T$ represents the sum concentration of $PbCO_3^0$ and potentially significant mixed ligand complexes such as $PbCO_3Cl^-$. The absorbance of Pb(II) in seawater can be described using the following equation (Byrne, 1981; Soli et al, 2008):

$$\frac{_\lambda A}{l \cdot [Pb]_T} = \frac{_\lambda \varepsilon_{Pb} + _\lambda \varepsilon_{PbCO3} \, _{CO3}\beta_1 [CO_3^{2-}]_T}{1 + _{CO3}\beta_1 [CO_3^{2-}]_T} \quad (3)$$

where $_\lambda A$ is the absorbance of Pb(II) at wavelength λ, l is the pathlength, $[Pb]_T$ is the total lead concentration, $_\lambda \varepsilon_{PbCO3}$ is the molar absorbance of $(PbCO_3^0)_T$ at wavelength λ, $_\lambda \varepsilon_{Pb}$ is the molar absorbance of $(Pb_T)$ at wavelength λ and $_{CO3}\beta_1$ is the formation constant of $PbCO_3^0$ as defined in Eq. (2). Eq. (3) can be used to describe the dependence of Pb(II) absorbance ($_\lambda A$) on $[CO_3^{2-}]_T$ and determine an internally consistent set of values for $_\lambda \varepsilon_{Pb}, _\lambda \varepsilon_{PbCO3}$ and $_{CO3}\beta_1$.

Use of Eq. (3) at wavelengths and allows carbonate ion concentrations, $[CO_3^{2-}]_T$, to be directly calculated from observations of absorbance ratios:

$$R = \frac{_{\lambda 2}A}{_{\lambda 1}A} = \frac{_{\lambda 2}\varepsilon_{Pb} + _{\lambda 2}\varepsilon_{PbCO3} \, _{CO3}\beta_1 [CO_3^{2-}]_T}{_{\lambda 1}\varepsilon_{Pb} + _{\lambda 1}\varepsilon_{PbCO3} \, _{CO3}\beta_1 [CO_3^{2-}]_T} \quad (4)$$

Rearrangement of Eq. (4) results in the following equation:

$$-\log[CO_3^{2-}]_T = \log_{CO3}\beta_1 + \log\left(\frac{R - e_1}{e_2 - R \cdot e_3}\right) \quad (5)$$

where $e_1$, $e_2$, and $e_3$ are Pb(II) molar absorbance ratios:

$$e_3 = _{\lambda 1}\varepsilon_{PbCO3} \quad (6)$$

The form of Eq. (5) is identical to that which has been used for highly precise measurements of seawater pH from observations of sulfonephthalein absorbance in seawater (Robert Baldo et al, 1985; Byrne, 1987; Byrne and Breland, 1989; Clayton and Byrne, 1993).

At sufficiently low pH (i.e., where $[CO_3^{2-}]_T \sim 0$), Eq. (4) can be written as:

$$R = _{\lambda 2}A/_{\lambda 1}A = _{\lambda 2}\varepsilon_{Pb}/_{\lambda 1}\varepsilon_{Pb} \quad (7)$$

It has been shown (Byrne et al., 1981) that characterizations of the molar absorptivities of individual species of Pb(II) can be used to directly determine the relative concentrations of $Pb^{2+}$, $PbCl^+$, $PbCl_2^0$ and $PbCl_3^-$ in both synthetic solutions and seawater. Since the relative concentrations of these species are directly dependent on the chloride concentrations in synthetic solutions and seawater, it follows that Pb(II) absorbance ratios at low pH are directly dependent on salinity. In addition to developing a direct means of determining carbonate ion concentrations via Eq. (5), we show in this work that observations of Pb(II) absorbance ratios at low pH allow calculations of seawater salinity with a precision somewhat better than ±0.2%.

Methods

Eq. (5) can be used to determine carbonate ion concentrations via direct measurements of Pb(II) absorbance ratios, and characterizations of $_{CO3}\beta_1$, $e_1$, $e_2$, and $e_3$. Observations of Pb(II) absorbance spectra at salinities typical of open ocean seawater (S=35.87) reveal isosbestic points near 234 nm (FIG. 1). On this basis, one of the two wavelengths chosen for absorbance observations was $\lambda_1$=234 nm. Although use of shorter wavelengths is desirable as a means of increasing sensitivity to formation of $PbCO_3^0$, small absorbance contributions from carbonate ions at shorter wavelengths make interpretations of absorbances at λ<234 nm less direct. In view of the substantial absorbance variations between 240 and 260 nm (FIG. 1), the second of the two wavelengths chosen for absorbance ratio observations was $\lambda_2$=250 nm.

Figure 2:
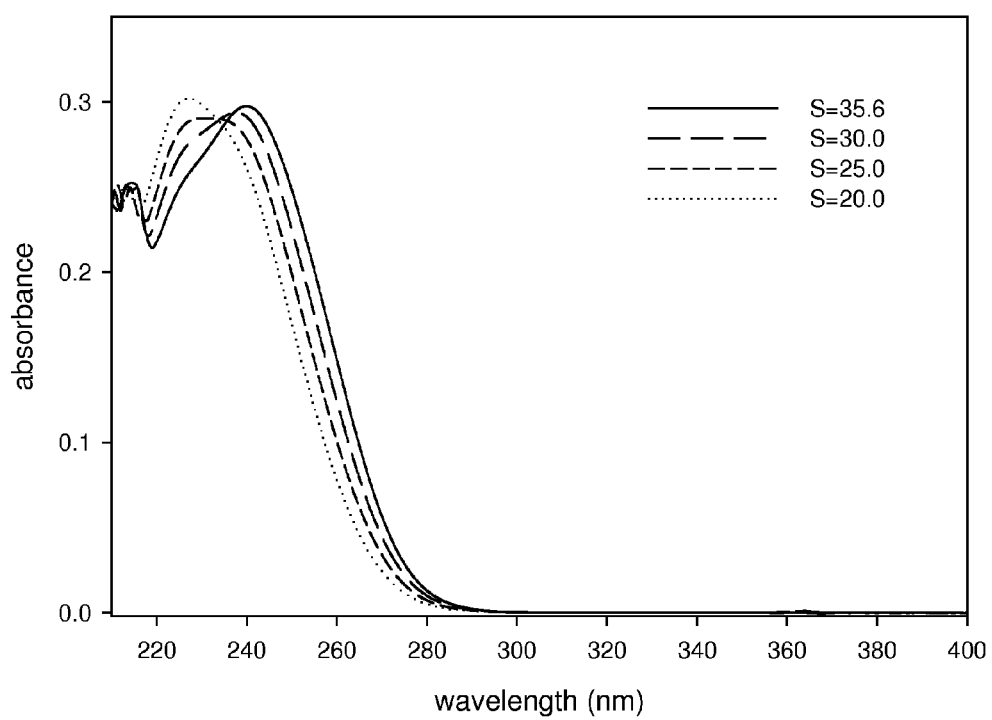
FIG. 2 is a graph showing Pb(II) UV absorbance spectra of acidified seawater (25° C., pH=3.73) at four selected salinities.

Characterizations of $\log _{CO3}\beta_1$ in this work were obtained using Eq. (3) and measurements of $_{250}A$ and $[CO_3^{2-}]_T$ in seawater samples at constant salinity and constant temperature. Along with characterizations of $\log _{CO3}\beta_1$, these measurements also produced paired characterizations of $_{250}\varepsilon_{Pb}$ and $_{250}\varepsilon_{PbCO3}$. Paired characterizations of $_{234}\varepsilon_{Pb}$ and $_{234}\varepsilon_{PbCO3}$ were obtained from measurements of $_{234}A$ and $[CO_3^{2-}]_T$ using Eq. (3), and the log $_{CO3}\beta_1$ values determined at each salinity, as described above. Paired characterizations of $_{234}\varepsilon_{Pb}$ and $_{250}\varepsilon_{Pb}$ were obtained from $_\lambda A$ observations at low pH (FIG. 2). The molar absorbance ratios $e_1$, $e_2$ and $e_3$ in Eq. (5) were then determined from these paired molar absorbance characterizations as follows:

$$e_1 = (_{250}\varepsilon_{PbCO3}/_{250}\varepsilon_{Pb}) \times (_{234}\varepsilon_{Pb}/_{234}\varepsilon_{PbCO3}) \times (_{250}\varepsilon_{Pb}/_{234}\varepsilon_{Pb}) \quad (8)$$

$$e_2 = (_{234}\varepsilon_{Pb}/_{234}\varepsilon_{PbCO3}) \times (_{250}\varepsilon_{Pb}/_{234}\varepsilon_{Pb}) \quad (9)$$

$$e_3 = (_{234}\varepsilon_{Pb}/_{234}\varepsilon_{PbCO3}) \quad (10)$$

All chemicals used were analytical reagent grade. $PbC_{12}$ and $NaHCO_3$ were from Sigma-Aldrich. HCl (1.000 M) was from J. T. Baker. The seawater used in this study was surface water from the Gulf of Mexico. Seawater salinity was measured with an SBE 49 CTD (Seabird). Seawater samples at various salinities were prepared by dilution with Milli-Q water. Absorbance measurements were obtained using quartz optical cells (10 cm pathlength) in an HP 8453 spectrophotometer. The slitwidth of this spectrophotometer is 1 nm. Use of a spectrophotometer with a substantially larger slitwidth can alter the wavelength-dependent absorbance characteristics of the parameters given in equations (8)-(10). The temperature of the samples in the optical cells was controlled (25±0.05)° C. with a Neslab refrigerating circulator and a water-jacketed spectrophotometric cell holder.

Seawater alkalinity was determined using a spectrophotometric procedure (Yao and Byrne, 1998) that is precise to better than 1 mmol/kg. Seawater (140.0 g) was added gravimetrically to an open top optical cell (10 cm pathlength) which, in turn, was positioned in the thermostated cell holder. Sample pH was measured using an Orion Ross-type pH electrode (No. 800500) connected to an Orion pH meter (Model 720A) in the absolute millivolt mode. Nerstian behavior of the pH electrode was confirmed via titrations of 0.7 molal NaCl solutions with concentrated HCl. The electrode was calibrated on the total hydrogen ion concentration scale through measurements in natural seawater whose pH was determined by simultaneous spectrophotometric observations of thymol blue absorbance ratios (Zhang and Byrne, 1996).

Through addition of $NaHCO_3$, the alkalinity of each seawater sample was increased to values approximately double those of natural seawater (final alkalinity ~4.0 millimolal). Seawater samples had $CO_2$ fugacities generally in excess of 500 μatm and pH≦8.0. After each seawater sample was thermally equilibrated, a reference spectrum was taken and 1.05 ml of a 0.001 mol/kg $PbCl_2$ stock solution was added to the sample (final $[Pb(II)]_T$~7.5 μmol $kg^{-1}$). An absorbance spectrum was then taken along with a potentiometric measurement of pH. The sample was subsequently titrated with standard HCl using a Gilmont micrometer syringe. HCl additions were quantified gravimetrically. Pb(II) absorbance, alkalinity and pH were recorded for each titration point. Sample alkalinity was calculated by accounting for cumulative HCl additions to the initial seawater sample. Calculations of $[CO_3^{2-}]_T$ from alkalinity and pH utilized the total $H^+$ scale dissociation constants of Dickson and Millero (1987) that were derived from the data of Mehrbach et al. (1973). All such calculations were performed using the $CO_2$ system program of Pierrot et al. (2006). Based on 95% confidence intervals for total alkalinities on the order of 0.1%, and 95% confidence intervals for open-cell pH measurements on the order of 0.01 units, corresponding relative errors in calculated carbonate ion concentrations are approximately 2.3% (e.g., ±5.8 μmol/kg when $[CO_3^{2-}]_T$=250 μmol/kg). Non-linear least squares parameter estimates of $_{80}\epsilon_{Pb}, _\lambda\epsilon_{PbCO3}$ and $_{CO3}\beta_1$ were obtained using Eq. (3) and paired values of $_\lambda A$ and $[CO_3^{2-}]_T$. Calculations of $[CO_3^{2-}]_T$ that accounted for minor contributions of $PbCO_3^0$ to carbonate alkalinity did not cause significant changes in derived values of $_\lambda\epsilon_{Pb}, _\lambda\epsilon_{PbCO3}$ and $_{CO3}\beta_1$. Absorbance contributions of $CO_3^{2-}$ at short wavelengths were examined by performing titration experiments without addition of Pb(II) to samples. Observations of well defined isosbestic points near λ=234 nm demonstrate that these corrections are very small at the wavelengths utilized in this work. The dependencies of $e_1$, $e_2$ and $e_3$ on salinity were described via quadratic functions.

Pb(II) absorbance measurements in acidified seawater (pH ~3.7, $[Pb(II)]_T$ ~7.5 μmol $kg^{-1}$) were used to determine $_\lambda\epsilon$ values at λ=234 and 250 nm. Absorbances, in this case, were measured against a reference solution of acidified seawater that contained no lead. The absorbance ratios obtained in these experiments ($_{250}\epsilon_{Pb}/_{234}\epsilon_{Pb}$) were used in determinations of $e_1$ and $e_2$, as described above, and were also used in a least squares quadratic regression that allows salinity (S) to be calculated from $_{234}A/_{250}A$ observations at low pH.

Results and Discussion

Figure 3:
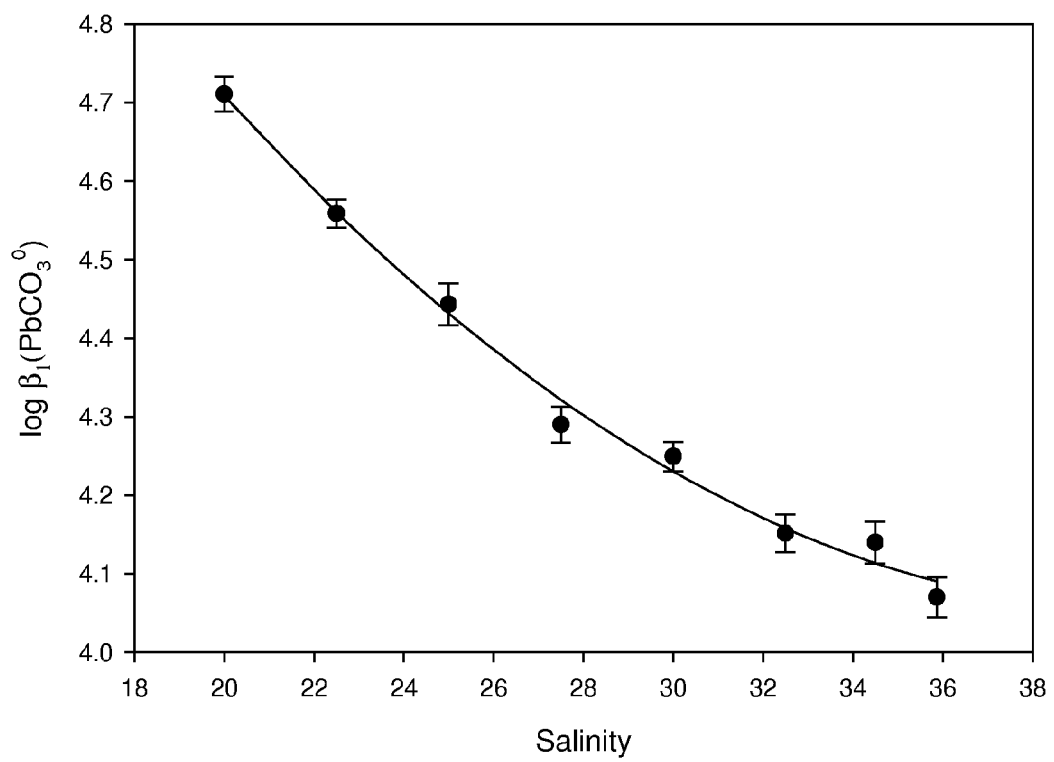
FIG. 3 is a graph showing salinity dependence of $PbCO_3^0$ formation constant at 25° C.
Figure 4A:
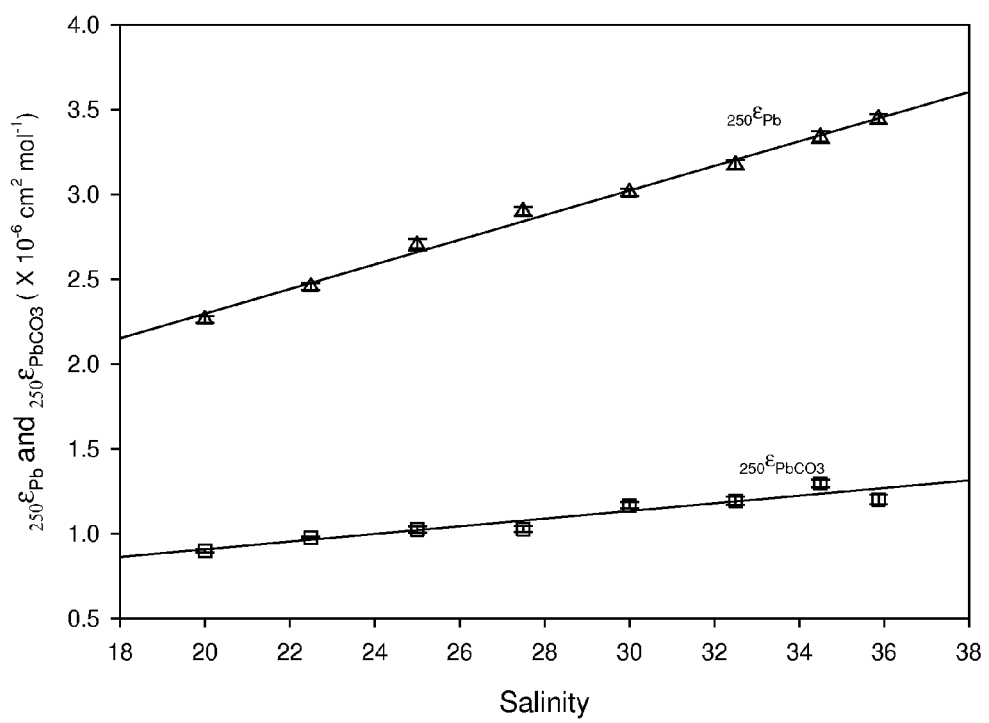
FIG. 4a is a graph showing salinity dependence of $_{250}\epsilon_{Pb}$ and $_{250}\epsilon_{PbCO_3}$ at 25° C.

Salinity Dependencies of Pb(II) Molar Absorptivities and the $PbCO_3^0$ Formation Constant Estimates for $_{CO3}\beta_1, _{250}\epsilon_{Pb}$ and $_{250}\epsilon_{PbCO3}$ obtained using Eq. (3) are given in Table 1 and are shown graphically in FIGS. 3 and 4a. Over a salinity range between S=20 and S=36, the dependence of the $PbCO_3^0$ formation constant on S at 25° C. (FIG. 3) can be described as:

$$\log{_{CO3}\beta_1} = 6.574 - 0.1235S + 1.514 \times 10^{-3}S^2 \tag{11}$$

with a ±0.023 standard error of estimation. The $_{250}\epsilon_{Pb}$, and $_{250}\epsilon_{PbCO3}$ values determined in this analysis exhibited a linear dependence on salinity:

$$_{250}\epsilon_{Pb} = 8.443 \times 10^5 + 7.258 \times 10^4 S \tag{12}$$

$$_{250}\epsilon_{PbCO3} = 4.563 \times 10^5 + 2.252 \times 10^4 S \tag{13}$$

Figure 4B:
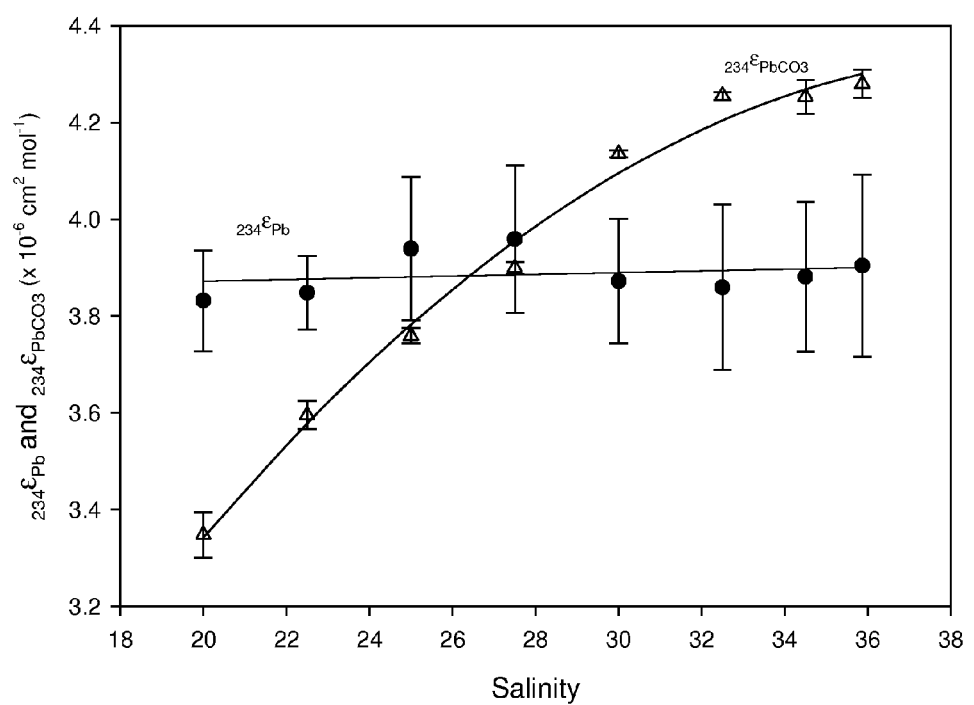
FIG. 4b is a graph showing salinity dependence of $_{234}\epsilon_{Pb}$ and $_{234}\epsilon_{PbCO_3}$ at 25° C.

The $_{234}\epsilon_{Pb}$ and $_{234}\epsilon_{PbCO3}$ values determined using the $\log{_{CO3}\beta_1}$ results in Table 1 and absorbance observations at 234 nm are given in Table 2. The FIG. 4b graphical depiction of these results shows that the dependence of $_{234}\epsilon_{Pb}$ on salinity is linear while satisfactory descriptions of $_{234}E_{PbCO3}$ require a quadratic term:

$$_{234}\epsilon_{Pb} = 3.837 \times 10^6 + 1.749 \times 10^3 S \tag{14}$$

$$_{234}\epsilon_{PbCO3} = 3.055 \times 10^5 + 2.028 \times 10^5 S - 2.548 \times 10^3 S^2 \tag{15}$$

TABLE 1

$PbCO_3^0$ formation constant ($_{CO3}\beta_1$), $_{250}\epsilon_{Pb}$, and $_{250}\epsilon_{PbCO3}$ as function of salinity at 25° C.

| Salinity | $\log{_{CO3}\beta_1}$ | $_{250}\epsilon_{Pb}$ ($\times 10^{-6}$ cm$^2$ mol$^{-1}$) | $_{250}\epsilon_{PbCO3}$ ($\times 10^{-6}$ cm$^2$ mol$^{-1}$) |
|---|---|---|---|
| 35.87 | 4.070 ± 0.030 | 3.445 ± 0.028 | 1.200 ± 0.028 |
| 34.50 | 4.140 ± 0.028 | 3.339 ± 0.035 | 1.297 ± 0.024 |
| 32.50 | 4.151 ± 0.026 | 3.176 ± 0.028 | 1.193 ± 0.025 |
| 30.00 | 4.249 ± 0.021 | 3.012 ± 0.021 | 1.167 ± 0.019 |
| 27.50 | 4.290 ± 0.024 | 2.900 ± 0.028 | 1.027 ± 0.019 |
| 25.00 | 4.443 ± 0.028 | 2.703 ± 0.032 | 1.024 ± 0.017 |
| 22.50 | 4.559 ± 0.018 | 2.455 ± 0.020 | 0.976 ± 0.008 |
| 20.00 | 4.711 ± 0.022 | 2.263 ± 0.021 | 0.899 ± 0.011 |

Figure 5:
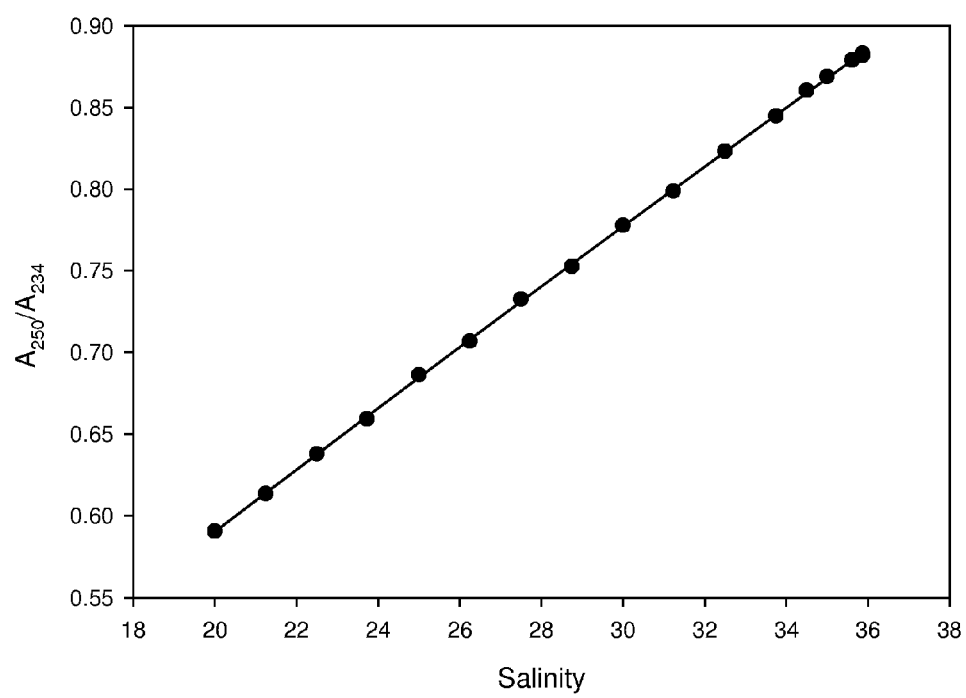
FIG. 5 is a graph showing Pb(II) absorbance ratios of in acidified seawater at 250 and 234 nm: $_{250}A/_{234}A$ ($_{250}\epsilon_{Pb}/_{234}\epsilon_{Pb}$) as a function of salinity.

The salinity dependence for observations of $_{250}\epsilon_{Pb}/_{234}\epsilon_{Pb}$ in acidified seawater (Table 3 and FIG. 5) is well described by the following expression:

$$_{250}\epsilon_{Pb}/_{234}\epsilon_{Pb} = 0.1931 + 2.062 \times 10^{-2}S - 3.852 \times 10^{-5}S^2 \tag{16}$$

Using the results that are summarized in Eqs. (12) through (16), Eqs. (8) through (10) can be used to calculate $e_1$, $e_2$ and $e_3$ at each salinity. The coefficients obtained in this manner are given in Table 4 and are depicted graphically in FIGS. (6a), (6b) and (6c).

The salinity dependencies of $e_1$, $e_2$ and $e_3$ are then given as follows:

$$e_1 = 0.3447 - 6.662 \times 10^{-3}S + 1.463 \times 10^{-4}S^2 \tag{17}$$

$$e_2 = 0.7749 - 1.122 \times 10^{-2}S + 3.331 \times 10^4 S^2 \tag{18}$$

$$e_3 = 2.114 - 6.600 \times 10^{-2}S + 9.036 \times 10^{-4}S^2 \tag{19}$$

TABLE 2

$_{234}\epsilon_{Pb}$ and $_{234}\epsilon_{PbCO3}$, as a function of salinity at 25 °C.

| Salinity | $_{234}\epsilon_{Pb}$ (×10$^{-6}$ cm$^2$ mol$^{-1}$) | $_{234}\epsilon_{PbCO3}$ (×10$^{-6}$ cm$^2$ mol$^{-1}$) |
|---|---|---|
| 35.87 | 3.904 ± 0.188 | 4.280 ± 0.029 |
| 34.50 | 3.881 ± 0.155 | 4.253 ± 0.035 |
| 32.50 | 3.859 ± 0.171 | 4.255 ± 0.008 |
| 30.00 | 3.872 ± 0.129 | 4.135 ± 0.007 |
| 27.50 | 3.959 ± 0.153 | 3.899 ± 0.012 |
| 25.00 | 3.939 ± 0.148 | 3.759 ± 0.016 |
| 22.50 | 3.848 ± 0.076 | 3.595 ± 0.029 |
| 20.00 | 3.832 ± 0.104 | 3.348 ± 0.047 |

TABLE 3

Absorbance of Pb(II) in acidified seawater (pH = 3.73): $_{250}A/_{234}A = _{250}\epsilon_{Pb}/_{234}\epsilon_{Pb}$ as function of salinity at 25° C.

| Salinity | $_{250}A/_{234}A$ ($_{250}\epsilon_{Pb}/_{234}\epsilon_{Pb}$) |
|---|---|
| 20.00 | 0.5906 |
| 21.25 | 0.6135 |
| 22.50 | 0.6380 |
| 23.73 | 0.6593 |
| 25.00 | 0.6863 |
| 26.25 | 0.7069 |
| 27.50 | 0.7327 |
| 28.75 | 0.7526 |
| 30.00 | 0.7778 |
| 31.24 | 0.7987 |
| 32.50 | 0.8231 |
| 33.75 | 0.8448 |
| 34.50 | 0.8603 |
| 35.00 | 0.8688 |
| 35.61 | 0.8788 |
| 35.87 | 0.8830 |
| 35.87 | 0.8818 |

Determinations of $CO_3^{2-}$ Concentrations in Seawater

Eq. (5), Eq. (11), and Eqs. (17) through (19) permit direct measurements of $[CO_3^{2-}]_T$ from measurements of Pb(II) absorbance ratios in seawater at 25° C. Eq. (5) can, however, also be written in an alternative form, with a smaller number of parameters:

$$-\log [CO_3^{2-}]_T = \log \{(_{CO3}\beta_1)/(e_2)\} + \log \{(R-e_1)/(1-Re_3/e_2)\} \quad (20)$$

Figure 6A:
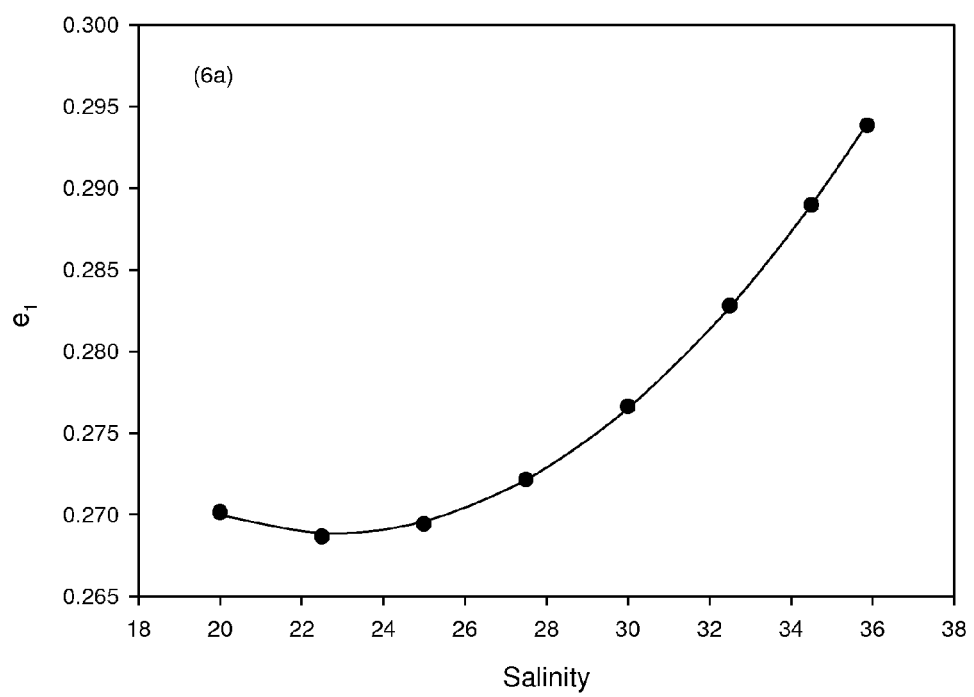
FIG. 6 is a series of three graphs showing salinity dependence of $e_1$ (6a), $e_2$ (6b), and $e_3$ (6c) at 25° C.
Figure 6B:
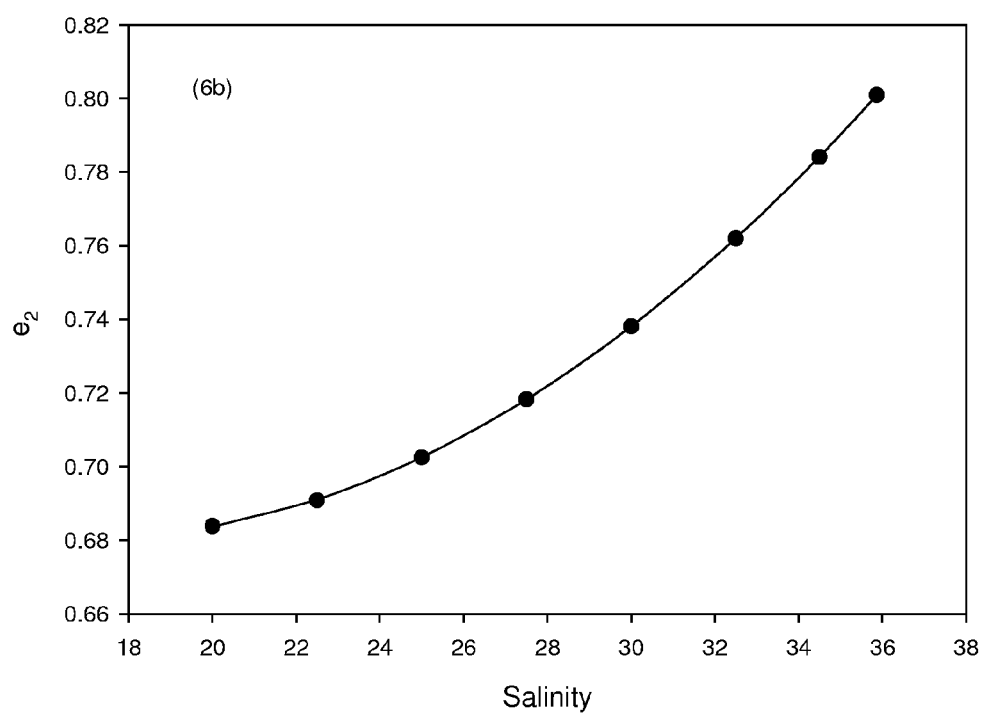
Figure 6C:
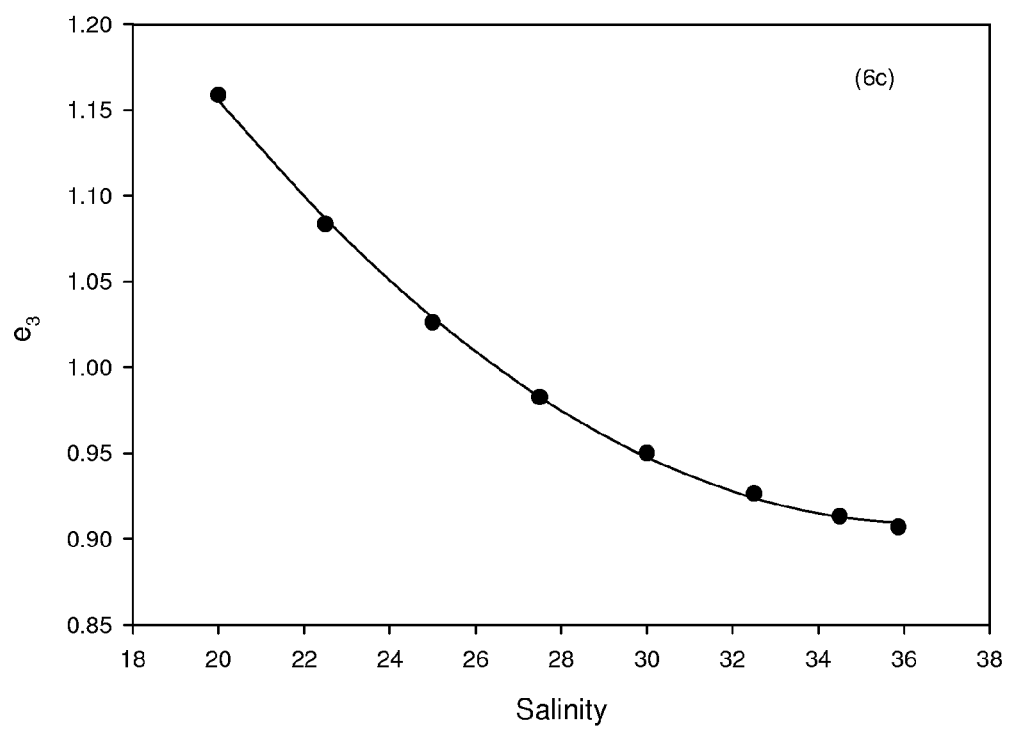
Figure 7A:
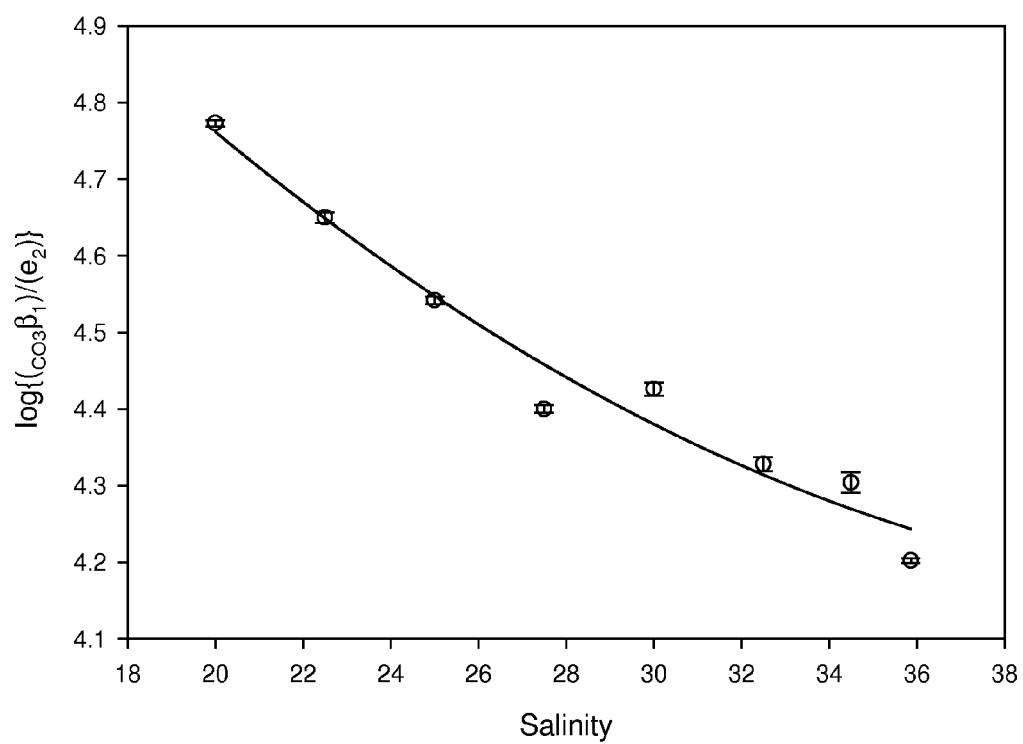
FIG. 7a is a graph showing the best fit log $\{(_{CO3}\beta_1)/(e_2)\}$ results using Eq. (20)
Figure 7B:
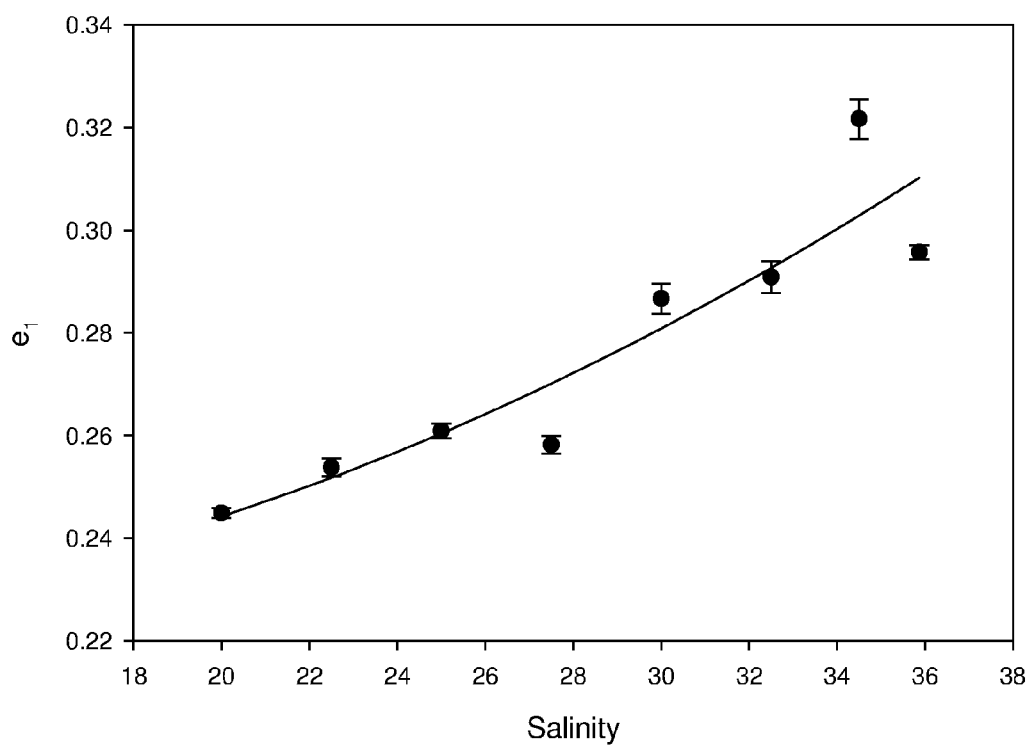
FIG. 7b is a graph showing the best fit $e_1$ results using Eq. (20).
Figure 8:
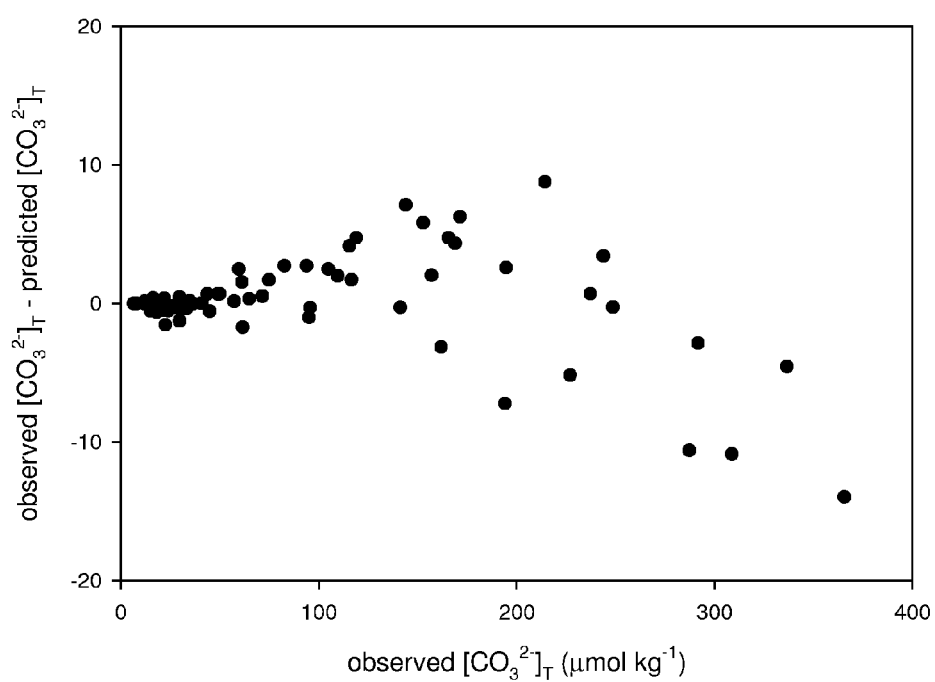
FIG. 8 is a graph showing residuals ($[CO_3^{2-}]_{observed} - [CO_3^{2-}]_{predicted}$) plotted as a function of ($[CO_3^{2-}]_{observed}$ for the least squares analyses using Eq. (20).

This equation is advantageous for calculations of carbonate ion concentrations because (a) it reduces the number of parameterizations required for measurements—Using Eq. (20), $(_{CO3}\beta_1)/(e_2)$ is determined as a single parameter, and $(e_3/e_2)$ is determined as a single parameter; (b) the parameter $(e_3/e_2)$ can be precisely determined from direct measurements at low pH—It is directly determined from the absorbance ratios shown in FIG. 6 ($(e_3/e_2) = (_{250}A/_{234}A)^{-1}$); (c) using $(e_3/e_2)$ values determined at low pH, Eq. (20) can be used with paired $[CO_3^{2-}]_T$ and R observations to directly determine $(_{CO3}\beta_1)/(e_2)$ and $e_1$. The results of such analyses, using each of the data sets that were employed to develop Eq. (11) and Eqs. (17) through (19), are given in Table 5 and are depicted graphically in FIGS. 7a and 7b. FIG. 8 shows the residuals, $([CO_3^{2-}]_T)_{observed} - ([CO_3^{2-}]_T)_{predicted}$, for each least squares analysis using Eq. (20). It should be noted that the residuals shown in FIG. 8 are derived from three independent sources. One of these is the absorbance ratios that are used to predict $[CO_3^{2-}]_T$ via Eq. (20), and the others are the alkalinity and pH measurements that are used to derive "observed" values of $[CO_3^{2-}]_T$. Of these three types of measurements, there is reason to suspect that potentiometric pH measurements may constitute the greatest source of scatter seen in FIG. 8. Since field measurements of $[CO_3^{2-}]_T$ based on absorbance ratios are independent of alkalinity and pH, the precision of $[CO_3^{2-}]_T$ measurements obtained via absorbance spectroscopy should be considerably better than that which is depicted in FIG. 8. The results shown in FIG. 8 suggest that Eq. (20) can be used to satisfactorily predict $[CO_3^{2-}]_T$ over a wide range of conditions in seawater. Preliminary assessment of the relative contributions of potentiometric and spectrophotometric contributions to the residuals in FIG. 8 suggest that the relative standard deviation for Eq. (20) calculations of $[CO_3^{2-}]_T$ is on the order of 2% or less. The best least squares descriptions for the salinity dependencies of the parameters in Eq. (20) for $20 \leq S \leq 36$ are given as follows:

$$\log \{(_{CO3}\beta_1)/(e_2)\} = 6.087 - 8.495 \times 10^{-2} S + 9.360 \times 10^{-4} \quad (21)$$

$$e_1 = 0.2215 - 5.554 \times 10^{-4} S + 8.440 \times 10^{-5} \quad (22)$$

$$(e_3/e_2) = 3.061 - 8.730 \times 10^{-2} S + 9.363 \times 10^{-4} \quad (23)$$

TABLE 4

$e_1$ ($_{250}\epsilon_{PbCO3}/_{234}\epsilon_{PbCO3}$), $e_2$ ($_{250}\epsilon_{Pb}/_{234}\epsilon_{PbCO3}$) and $e_3$ ($_{234}\epsilon_{Pb}/_{234}\epsilon_{PbCO3}$) as a function of salinity at 25° C.

| Salinity | $e_1$ | $e_2$ | $e_3$ |
|---|---|---|---|
| 35.87 | 0.2938 | 0.8009 | 0.9068 |
| 34.50 | 0.2890 | 0.7841 | 0.9131 |
| 32.50 | 0.2828 | 0.7619 | 0.9263 |
| 30.00 | 0.2766 | 0.7381 | 0.9498 |
| 27.50 | 0.2721 | 0.7182 | 0.9825 |
| 25.00 | 0.2694 | 0.7024 | 1.0262 |
| 22.50 | 0.2687 | 0.6908 | 1.0835 |
| 20.00 | 0.2701 | 0.6838 | 1.1588 |

TABLE 5

Best fit $\log\{(_{CO3}\beta_1)/(e_2)\}$ and $e_1$ results obtained using Eq. (20). The $(e_3/e_2)$ values used in Eq. (20) are the reciprocals of the $_{250}A/_{234}A$ values given in Table 3.

| Salinity | $\log\{(_{CO3}\beta_1)/(e_2)\}$ | $e_1$ |
|---|---|---|
| 35.87 | 4.202 | 0.2957 |
| 34.50 | 4.304 | 0.3217 |
| 32.50 | 4.328 | 0.2909 |
| 30.00 | 4.426 | 0.2867 |
| 27.50 | 4.400 | 0.2582 |
| 25.00 | 4.542 | 0.2609 |
| 22.50 | 4.650 | 0.2538 |
| 20.00 | 4.773 | 0.2449 |

It should be emphasized that the equation (22) and (23) characterizations of $e_1$ and $e_3/e_2$ were obtained through fits involving equation (20) and did not involve the $e_1$, $e_2$ and $e_3$ characterizations given in equations (17) through (19).

Using equations (20) through (23) carbonate ion concentrations can be measured via procedures that closely follow those employed by Clayton and Byrne (1993) for measurements of seawater pH:

Seawater obtained from Niskin bottles is transferred directly to 10 cm quartz cuvettes without exposure to the atmosphere (samples are not filtered).

Samples in the quartz cuvettes (total volume ~30 cm$^3$) are thermostatted at 25° C.

The thermostatted sample is directly used as a reference (baseline) solution ($_\lambda A = 0$ at all wavelengths). Note, in this case, that absorbance contributions from UV active species such as nitrate are identical in the reference (baseline) measurement and in subsequent measurements wherein Pb(II) is added to the solution. As such, the absorbance contributions of such species (nitrate, organics etc.) are eliminated via baseline subtraction.

A 1 mM stock solution of $PbCl_2$ is added to the cuvette (~0.22 cm$^3$ addition) whereupon the Pb(II) concentration is approximately 7.5 μM.

Absorbances are measured at 234, 250 and 350 nm, and the absorbance at λ=350 nm is used to correct for any small baseline changes induced by manipulation of the cuvette.

Using the absorbance ratio obtained through this protocol ($_{250}A/_{234}A$), and the salinity dependent coefficients in equations 21-23, equation 20 is used to calculate log $[CO_3^{2-}]_T$.

It should be noted that the relatively high lead concentrations used for measurements of carbonate ion concentrations preclude significant complexation by dissolved and particulate organics in seawater. Since ionic Pb(II) in seawater is not significantly volatile, the principal safety concern surrounding the manipulation of solutions enriched in lead is avoidance of inadvertent ingestion. This should especially be borne in mind with respect to handling of the 1 mM stock Pb titrant solution and safe disposal of waste solutions.

Determinations of Seawater Salinity

Salinity measurements required for calculations of log $\{(_{CO3}\beta_1)/(e_2)\}$, $e_1$, and $(e_3/e_2)$ are commonly available from either shipboard or in situ conductimetric observations. When such is not the case, however, salinity can be calculated from absorbance ratios using the following relationship that is based on the data shown in FIG. 5 for acidified seawater:

$$S=-8.76+45.15R+6.092R^2 \quad (24)$$

where $R=_{250}A/_{234}A$ and $20 \leq S \leq 36$. The standard deviation for Eq. (24) estimates of salinity is ±0.06 salinity units. Thus, Eq. (24) provides seawater salinity estimates that are precise to approximately 0.2% over the normal salinity range of seawater.

Thus, salinity can be measured from absorbance ratio observations after Pb(II) is added to an acidic seawater solution. Other metals can be used to obtain sensitive salinity measurements over various ranges of salinity. The work reported herein was performed at 25° C. It follows that the salinity measurements could be performed at other temperatures after suitable laboratory calibrations. This would allow salinity measurements and/or carbonate measurements to be obtained without thermostatting. Such calibrations facilitate carbonate measurements in situ over a range of temperatures.

Potentiometric pH Measurements and Systems Calibration

The potentiometer measures the millivolts developed by a pH electrode vs a reference electrode. The solution measured consists of the aqueous medium plus a small amount of indicator. The pH of this mixture is assessed by both the spectrophotometer and the potentiometer. The potentiometric pH is determined by an equation of the following form:

$$pH=a+b\cdot(\text{millivolts}) \quad (25)$$

The "b" term in the above equation (Eq. 25) is an electrode slope that depends on temperature. The "a" term depends on a number of variables and can be determined via calibrations. In the present instance, the potentiometric system (or the calibration system) is "told" the pH of a given solution (i.e., the pH value is determined spectrophotometrically) whereupon the constant "a" is determined from the above equation. In such a system it is also possible to have an additional pump so that aqueous solution, indicator and acid are combined. In this case pH is again measured spectrotometrically and the above equation can be used to solve for both slope "b" and intercept "a".

CONCLUSIONS

In the absence of direct spectrophotometric determinations of $[CO_3^{2-}]_T$ as described above, $[CO_3^{2-}]_T$ must be calculated from measurements of either total dissolved inorganic carbon or total alkalinity combined with either pH or $CO_2$ fugacity. While spectrophotometric pH measurements are rapid, with acquisition rates on the order of seconds, measurements of dissolved inorganic carbon, total alkalinity and $CO_2$ fugacity generally require several minutes (as a lower bound). Thus, the spectrophotometric procedures for measurements of carbonate ion concentrations described in this work, and those for spectrophotometric pH analysis (Liu, et al., 2006), are unique in their suitability for prompt in situ analysis. Although, in situ analysis will require evaluations of the influence of temperature on the various parameters in Eq. (20), the work of Soli et al. (2008) showed that the influence of temperature on $\log(_{CO3}\beta_1)$ is quite small. Since the influence of temperature on molar absorptivity ratios should be relatively minor, it is likely that Eq. (20) can easily be extended to include analysis at in situ conditions. With respect to both in situ and laboratory analysis, spectrophotometric pH and $[CO_3^{2-}]_T$ measurement procedures can be distinguished from those required for $C_T$ with respect to both procedural and instrumental simplicity. In contrast to the equipment required for state of the art $C_T$ analyses, spectrophotometers are standard equipment in a wide variety of research and teaching laboratories.

As has been the case for spectrophotometric measurements of pH, it should be anticipated that the parameters required for quantitative $[CO_3^{2-}]_T$ measurements (e.g., Eqs. (21) through (24)) will periodically be reevaluated and refined. This process will include, in particular, comparisons obtained through ship-based oceanic carbon system expeditions wherein the thermodynamic consistency of all measurable $CO_2$ system parameters is commonly evaluated (Clayton et al., 1995; Lee et al., 2000). It should be emphasized in this case that any future revisions in characterizations of log $\{(_{CO3}\beta_1)/(e_2)\}$, $e_1$ and $(e_3/e_2)$ will allow refinements, with improved accuracy, of archived $[CO_3^{2-}]_T$ data. As long as data are recorded as R—S pairs (i.e., absorbance ratios and salinity), all calculations of $[CO_3^{2-}]_T$ are amenable to quantitative reassessment. As such, observations of Pb(II) absorbance ratios provide a molecularly-based index of carbonate ion concentrations in seawater.

The procedures described in this work are suitable for rapid, quantitative assessments of calcite and aragonite saturation states in seawater. Since the solubility products of calcite and aragonite in S=35 seawater are approximately $10^{-6.367}$ and $10^{-6.186}$ (Millero, 2007), and the total calcium concentration is 0.0103 mol/kg at salinity 35, the carbonate ion concentrations for saturation with calcite and aragonite are 41.7 μmol/kg and 63.3 μmol/kg. The log $_{CO3}\beta_1$ results given by Eq. (11) (log $_{CO3}\beta_1$=4.106 at S=35) show that inorganic Pb(II) is partitioned equally between $PbCO_3^0$ and lead chloride complexes when $[CO_3^{2-}]_T$=78.3 mmol/kg. Thus, the procedures described in this work are well suited to measurement of $CaCO_3$ saturation states both below and well above the saturation levels of calcite and aragonite.

REFERENCES

Acker, J. G.; Byrne, R. H.; Ben-Yaakov S.; Feely, R. A.; Betzer, P. R., 1987. The effect of pressure on aragonite dissolution rates in seawater. Geochim et Cosmochim Acta, 51, 2171-2175.

Broecker, W. S., Takahashi, T.; Simpson, H. J; Peng, T.-H., 1979. Fate of fossil fuel carbon dioxide and the global carbon budget. Science, 206, 409-418.

Byrne, R. H., 1981. Inorganic lead complexation in natural seawater determined by UV spectroscopy. Nature, 290, 487-489.

Byrne, R. H.; Miller W. L., 1985. Copper(II) carbonate complexation in seawater. Geochim et Cosmochim Acta, 49, 1837-1844.

Byrne, R. H., 1987. Standardization of standard buffers by visible spectrometry. Anal. Chem. 59, 1479-1481.

Byrne, R. H.; Breland, J. A., 1989. High precision multiwavelength pH determinations in seawater using cresol red. Deep-Sea Res. A. 36, 803-810.

Byrne, R. H., 2002. Inorganic speciation of dissolved elements in seawater: the influence of pH on concentration ratios. Geochem. Trans. 3, 11-16.

Byrne, R. H.; Young, R. W.; Miller, W. L., 1981. Lead chloride complexation using ultraviolet molar absorptivity characteristics. J. Sol. Chem. 4, 243-251.

Cantrell, K. J.; Byrne R. H., 1987. Rare earth element complexation by carbonate and oxalate ions. Geochim et Cosmochim Acta, 51, 597-605.

Clayton, T. D.; Byrne, R. H., 1993. Spectrophotometric seawater pH measurements: total hydrogen ion concentration scale calibration of m-cresol purple and at-sea results. Deep-Sea Res. A. 40, 2115-2129.

Clayton, T. D.; Byrne, R. H.; Breland, J. A.; Feely, R. A.; Millero, F. J.; Campbell, D. M.; Murphy, P. R.; Lamb, M. F., 1995. The role of pH measurements in modern $CO_2$-system characterization: precision and thermodynamic consistency. Deep Sea Res. 42, 411-429.

Dickson, A G; Millero, F. J., 1987. A comparison of the equilibrium constants for the dissociation of carbonic acid in seawater media. Deep-Sea Res. 34, 1733-1743.

DOE 1994. Handbook of Methods, Version 2, A. G. Dickson & C. Goyet, eds. ORNL/CDIAC-74.

Feely, R. A.; Sabine, C. L.; Lee, K.; Berelson, W.; Kleypas, J.; Fabry, V. J.; Millero, F. J., 2004 Impact of anthropogenic $CO_2$ on the $CaCO_3$ system in the oceans. Science, 305, 362-366.

Keir, R. S., 1980. The dissolution kinetics of biogenic calcium carbonates in seawater. Geochim Cosmochim Acta, 44, 241-252.

Kleypas, J. A.; Feely, R. A.; Fabry, V. J., Langdon, C.; Sabine, C. L.; Robbins, L. L., 2006. Impacts of Acidification on Coral Reefs and Other Marine Calcifiers: A guide for future research. Report of a workshop held 18-20 Apr. 2005, St. Petersburg Fla., sponsored by NSF, NOAA and U.S. Geological Survey. 88 pp.

Langdon, C.; Atkinson, M. J., 2005. Effect of elevated $pCO_2$ on photosynthesis and calcification of corals and interactions with seasonal change in temperature/irradiance and nutrient enrichment. J. Geophys. Res. 110, C09S05, doi:10.1029/2004JC002576.

Lee, K.; Millero, F. J.; Byrne, R. H.; Feely, R. A.; Wanninkhof, R., 2000. The recommended dissociation constants for carbonic acid in seawater. Geophys. Res. Lett. 27, 229-232.

Liu, X.; Wang, Z. A.; Byrne, R. H.; Kaltenbacher, E. A.; Bernstein, R. E., 2006. Spectrophotometric measurements of pH in-situ: laboratory and field evaluations of instrumental performance. Environ. Sci. Tech. 40, 5036-5044.

McGillis, W. R.; Wanninkhof, R., 2006. Aqueous $CO_2$ gradients for air-sea flux estimates. Mar. Chem. 98, 100-108.

Mehrbach,; Culberson, C. H.; Hawley, J. E.; Pytkowicz, R. M., 1973. Measurement of the apparent dissociation constants of carbonic acid in seawater at atmospheric pressure. Limnol. Oceanogr. 18, 897-907.

Millero, F. J., 2007. The marine inorganic carbon cycle. Chem. Rev. 107, 308-341.

Morse, J. W., 1978. Dissolution kinetics of calcium carbonate in sea water; VI, The near-equilibrium dissolution kinetics of calcium carbonate-rich deep sea sediments. Amer. J. Sci. 278, 344-355.

Orr, J. C.; Fabry, V. J.; Aumont, O.; Bopp, L.; Doney, S. C.; Feely, R. A.; Gnanadesikan, A.; Gruber, N.; Ishida, A.; Joos, F.; Key, R. M.; Lindsay, K.; Maier-Reimer, E.; Matear, R.; Monfray, P.; Mouchet, A.; Najjar, R. G.; Plattner, G.-K; Rodgers, K. B.; Sabine, C. L.; Sarmiento, J. L.; Schlitzer, R.; Slater, R. D.; Totterdell, I. J.; Weirig, M.-F; Yamanaka, Y.; Yool, A., 2005. Anthropogenic ocean acidification over the twenty-first century and its impact on calcifying organisms. Nature, 437, 681-686.

Pierrot, D.; Lewis, E.; Wallace, D. W. R. 2006. MS Excel Program Developed for $CO_2$ System Calculations. ORNL/CDIAC-105. Carbon Dioxide Information Analysis Center, Oak Ridge National Laboratory, U.S. Department of Energy, Oak Ridge, Tenn.

Robert-Baldo, G.; Morris, M. J.; Byrne, R. H., 1985. Spectrophotometric determination of seawater pH using phenol red. Anal. Chem. 57, 2564-2567.

Royal Society, 2005. Ocean Acidification due to Increasing Atmospheric Carbon Dioxide. *Policy Document 12/05, The Royal Society.*

Soli, A. L.; Stewart, Z. I.; Byrne, R. H., 2008. The influence of temperature on $PbCO_3^0$ formation in seawater. Mar. Chem. 110, 1-6.

Yao, W.; Byrne, R. H., 1998. Simplified seawater alkalinity analysis: use of linear array spectrometers. Deep-sea Res. 45, 1383-1392.

Zhang, H.; Byrne, R. H., 1996. Spectrophotometric pH measurements of surface seawater at in-situ conditions: absorbance and protonation behavior of thymol blue. Mar. Chem. 52, 17-25.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of performing in situ continuous autonomous potentiometric pH measurements for extended periods of time comprising the steps of:
   recording a plurality of potentiometric pH measurements using a potentiometric pH measurement device;
   autonomously activating a spectrophotometric calibration system positioned within the device wherein the system is activated by an event trigger or a defined time interval wherein the event trigger is a sudden pH change outside the typical deviations of pH recordings;
   calibrating the potentiometric pH measurement device comprising the steps of:
      obtaining spectrophotometric pH measurements from a spectrophotometer located within the device comprising the steps of:
         sampling an aqueous medium;

collecting data representative of temperature and salt concentration of the sampled aqueous medium;

combining a sulfonephthalein indicator and a first portion of the sampled aqueous medium;

delivering the combined medium to an optical cell;

obtaining an absorbance spectrum from the combined medium;

calculating solution pH of the sampled aqueous medium utilizing the optical absorbance ratios at multiple wavelengths, the temperature, and the salt concentration;

obtaining a potentiometric pH measurement of a second portion of the aqueous medium substantially contemporaneously with the spectrophotometric pH measurements;

calculating the deviation between the potentiometric pH measurement and the spectrophotometric pH measurement; and adjusting the potentiometric pH measurement device using the calculated deviation, wherein the adjusting calibrates the potentiometric pH measurement device; and recording the calibrated potentiometric pH measurements for an extended period of time until an event trigger or preset time interval autonomously activates the spectrophotometric calibration system to calibrate the device.

2. The method of claim 1 wherein measurement frequency of the potentiometric pH measurement is 60 Hz or below.

* * * * *